United States Patent [19]
Wayne et al.

[11] Patent Number: 5,866,422
[45] Date of Patent: Feb. 2, 1999

[54] METHOD FOR CLONING AND PRODUCING THE TSP45I RESTRICTION ENDONUCLEASE IN E. COLI

[75] Inventors: Jay Wayne, Flushing, N.Y.; Shuang-yong Xu, Lexington, Mass.

[73] Assignee: New England Biolabs, Inc., Beverly, Mass.

[21] Appl. No.: 960,756

[22] Filed: Oct. 29, 1997

[51] Int. Cl.⁶ ............................ C12N 15/54; C12N 15/55
[52] U.S. Cl. .................... 435/428; 435/193; 435/194; 435/320.1; 536/23.2
[58] Field of Search .................................. 435/199, 193, 435/320.1, 478; 536/23.2

[56] References Cited

PUBLICATIONS

Blumenthal, et al. J. Bacter., 164:501–509 (1985).
Bougueleret, et al., Nucl. Acids Res., 12:3659–3676 (1984).
Brenner, et al., Nucl. Acids Res., 18:355–359 (1990).
Coolbear, et al., Adv. Biochem. Eng. Biotech. 45:57–98 (1992).
Cowan, Biochem. Soc. Symp. 58:149–169 (1992).
Eberhard, et al., Plasmid 6:1–6 (1981).
Fomenkov, et al. Nucl. Acids Res. 22:2399–2403 (1994).
Gingeras and Brooks, Proc. Natl. Acad. Sci. USA 80:402–406 (1983).
Hishinuma, et al., J. Gen. Microbiol. 104:193–199 (1978).
Hjorleifsdottir, et al., Biotech. Tech. 10:13–18 (1996).
Ishida and Oshima, J. Bacteriol. 176:2767–2770 (1994).
Kirino, et al., Eur. J. Biochem., 220–275–281 (1994).
Kiss, et al. Nucl. Acids Res. 13:6403–6419 (1985).
Kong, et al., J. Biol. Chem., 268:1965–1975 (1993).
Kosykh, et al. Molec. Gen. Genet., 178:717–718 (1980).
Koyoma, et al., J. Bacteriol., 166:338–340 (1986).
Koyoma, et al., FEMS Microbiol. Lett, 72:97–102 (1990).
Kristjansson and Stetter, in 'Thermophilic Bacteria', Kristjansson, ed. 1–18 (1992).
Kristjansson, Trends Biotech. 7:349–353 (1989).
Lasa, et al., J. Bacteriol. 174:6424–6431 (1992).
Mann, et al., Gene, 3:97–112 (1978).
Maseda and Hoshino, FEMS Microbiol. Lett. 128:127–134 (1985).
Moriyama, et al. J. Biochem., 117:408–413 (1985).
Munster, et al., Appl. Environ. Microbiol., 50:1325–1327 (1985).
Nolling and DEVos, J. Bacteriol., 17:5719–5726 (1992).
Numata, et al., Prot. Eng. 8:39–43 (1995).
Raven, et al. Nucl. Acids Res., 21:4397 (1993).
Wayne an Xu, Gene 195:321–328 (1997).
Roberts and Halford, in 'Nucleases', 2nd ed. Linn, et al. ed's. pp. 35–88 (1993).
Roberts and Macelis, Nucl. Acids Res. 25:248–262 (1997).
Saskai and Oshima, J. Virol. 15:1449–1453 (1975).
Smith and Nathans, J. Mol. Biol., 81:419–423 (1973).
Theriault and Roy, Gene, 19:355–359 (1982).
Vasquez, et al., FEBS Lett. 158:339–342 (1983).
Walder, et al., Proc. Natl. Acad. Sci. USA, 78:1503–1507 (1981).
Wiegel and Ljungdahl, CRC Crit. Rev. Biotech. 3:39–108 (1984).
Wilson and Murray, Annu. Rev. Genet. 25:585–627 (1991).
Wilson, Nucl. Acids Res., 19:2539–2566 (1991).

*Primary Examiner*—Charles L. Patterson, Jr.
*Attorney, Agent, or Firm*—Gregory D. Williams

[57] ABSTRACT

The present invention relates to recombinant DNA molecules encoding the Tsp45I gene (tsp45IR), and the cognate M.Tsp45I gene (tsp45IM), from *Thermus species* YS45 introduced into *E. coli* as well as expression of the recombinant Tsp45I restriction endonuclease in *E coli*.

12 Claims, 6 Drawing Sheets

FIG. 1A

```
                10                       30                      50
ATGAGCCGTAGCTACCCTGGTTTGACCCGAAAAGCCCCCTTGAAAGCCTCGAAAACCTCG
MetSerArgSerTyrProGlyLeuThrArgLysAlaProLeuLysAlaSerLysThrSer 70                       90                     110
GAACCTTCGCCCTTTAGGTTGGTCTACCCCGGAAAACGCGATGAGAAGGAGATTCTTGAT
GluProSerProPheArgLeuValTyrProGlyLysArgAspGluLysGluIleLeuAsp 130                      150                     170
CAGCCCACCCCACAACTTGTTTTGCGAAAAGAAACCCTCCTCTTCCTAGGGGGAAATGCC
GlnProThrProGlnLeuValLeuArgLysGluThrLeuLeuPheLeuGlyGlyAsnAla 190                      210                     230
CCCCTTTTTGAGATTGATCCTATTGGCACCTACTTTTTGGGGGAAAACGGTCAGGTTCTC
ProLeuPheGluIleAspProIleGlyThrTyrPheLeuGlyGluAsnGlyGlnValLeu 250                      270                     290
CGGTGGATGCTCCGGGAGCCTGGTGGGTATGCGGGGAAGGTCCAGTTGGTCTATATTGAC
ArgTrpMetLeuArgGluProGlyGlyTyrAlaGlyLysValGlnLeuValTyrIleAsp 310                      330                     350
CCGCCTTATGGAACCGGCCAGCAGTTTCTCGTTGGCGGCGATGAAACAGATCGCGTTGCT
ProProTyrGlyThrGlyGlnGlnPheLeuValGlyGlyAspGluThrAspArgValAla 370                      390                     410
ACCGTCAGCCAGCCCAAAAACGGTCAGTTGGGCTACGATGACACCCTCGATGGTCCTCAG
ThrValSerGlnProLysAsnGlyGlnLeuGlyTyrAspAspThrLeuAspGlyProGln 430                      450                     470
TTTGTGGAGTTCCTGAGGGAGCGCTTGATACTTCTCAGGGAGCTGATGGCGGACTCAGGA
PheValGluPheLeuArgGluArgLeuIleLeuLeuArgGluLeuMetAlaAspSerGly 490                      510                     530
CTGATCTTCGTTCACATAGACGAGAAATACGGGTTCGAGGTGAAGCTCATCCTTGATGAG
LeuIlePheValHisIleAspGluLysTyrGlyPheGluValLysLeuIleLeuAspGlu 550                      570                     590
GTCTTTGGCCGGCGAAACTTCGTTAACCATATCGCCCGCATCGCTTCAAATCCCAAAAAC
ValPheGlyArgArgAsnPheValAsnHisIleAlaArgIleAlaSerAsnProLysAsn 610                      630                     650
TTTTCCCGTAAGGCCTTCGGATCGCAAAAGGACATGATCCTCGTCTACTCCAAAACGCGG
PheSerArgLysAlaPheGlySerGlnLysAspMetIleLeuValTyrSerLysThrArg 670                      690                     710
GACTACGTTTGGAACGAATCGGCTAGCCCCTATTCGGAAGAGGAGATCGCTAGGCTTTTC
AspTyrValTrpAsnGluSerAlaSerProTyrSerGluGluGluIleAlaArgLeuPhe 730                      750                     770
CCCTTTGTAGACGAGAACGGGGAACGGTACACCACCAATCCCCTGCATGCTCCTGGAGAA
ProPheValAspGluAsnGlyGluArgTyrThrThrAsnProLeuHisAlaProGlyGlu
```

FIG. 1B

```
          790                     810                      830
           .                       .                        .
ACCAAGGATGGCCCTACCGGAAGGCCTTGGCGAGGAATACTTCCCCCTCCTGGACGGCAT
ThrLysAspGlyProThrGlyArgProTrpArgGlyIleLeuProProProGlyArgHis 850                     870                      890
           .                       .                        .
TGGCGCTATCCCCCGGAGAAGCTTGACGAGCTAGACGCTCAAGGGCTTATTGTCTGGTCA
TrpArgTyrProProGluLysLeuAspGluLeuAspAlaGlnGlyLeuIleValTrpSer 910                     930                      950
           .                       .                        .
AAGAACGGGGTGCCGCGGAAGAAAGTTTACGCTCGGGATCGCCTGAAGAAGGGGAAGAAG
LysAsnGlyValProArgLysLysValTyrAlaArgAspArgLeuLysLysGlyLysLys 970                     990                     1010
           .                       .                        .
CTCCAGGACGTTTGGCAGTTCAAGGATCCTCCGTACCCGCGATACCCCACCGAGAAAAAT
LeuGlnAspValTrpGlnPheLysAspProProTyrProArgTyrProThrGluLysAsn 1030                    1050                     1070
           .                       .                        .
CTGGACATGCTCAAGCTCATCGTCCAAACAGGGAGTAACGAGGGGGATTTAGTGCTCGAT
LeuAspMetLeuLysLeuIleValGlnThrGlySerAsnGluGlyAspLeuValLeuAsp 1090                    1110                     1130
           .                       .                        .
CCCTTCGCAGGCTCCGGTACTACGCTTATAGCCTCACCCCTCTTAAAGCGGCGATCCATC
ProPheAlaGlySerGlyThrThrLeuIleAlaSerProLeuLeuLysArgArgSerIle 1150                    1170                     1190
           .                       .                        .
GGCATAGATGCCTCCTGGGAGGCGGTCAAAGCCTTCACTAGAAGGGTGTTAGAGGATTTC
GlyIleAspAlaSerTrpGluAlaValLysAlaPheThrArgArgValLeuGluAspPhe 1210                    1230
           .                       .
CCCAGGCTACAGCACAAGTTTGAGATTGTGTCCGCCTTCTAG
ProArgLeuGlnHisLysPheGluIleValSerAlaPheEnd
```

FIG. 2A

```
        10                    30                    50
ATGCAACAGATGGCCGAGTGGAACGTGTGGACACAGAGAAGCGTTGAGCTTCTGGAGAAG
MetGlnGlnMetAlaGluTrpAsnValTrpThrGlnArgSerValGluLeuLeuGluLys 70                    90                   110
GGGTATTTGGATAAACTACTGCAGGTCTATAAAGGGGAAAGTGGCTCTTCGAGGTCAGTA
GlyTyrLeuAspLysLeuLeuGlnValTyrLysGlyGluSerGlySerSerArgSerVal 130                   150                   170
CCAGAGGAGGTAGAGGAAAAACTTCGCGAGGCCTACAAGGCATACGAGGGGAGGCAGGAT
ProGluGluValGluGluLysLeuArgGluAlaTyrLysAlaTyrGluGlyArgGlnAsp 190                   210                   230
AGTCCGGAGGCAGAAACGAAACTCGTGGAAGCCGTGCTAAATGCCAGAAAAAAGGTCGAG
SerProGluAlaGluThrLysLeuValGluAlaValLeuAsnAlaArgLysLysValGlu 250                   270                   290
CGGTCCCCCTTCAATCACCCCTACCTGCCTTTGGTCTACTACCTGGTTTCGGAAAAAGCA
ArgSerProPheAsnHisProTyrLeuProLeuValTyrTyrLeuValSerGluLysAla 310                   330                   350
GAAAAAGCGAACAAGGCCCTTGAGGAGGCATTGCAGGAGGTTGCCTCAAAGCACCCAGAA
GluLysAlaAsnLysAlaLeuGluGluAlaLeuGlnGluValAlaSerLysHisProGlu 370                   390                   410
ACCATCCGCGTCCTGGCCAAGGAAGCGCAAAGAAGAGGCGTAGAAGCCTTGATCCAAAGG
ThrIleArgValLeuAlaLysGluAlaGlnArgArgGlyValGluAlaLeuIleGlnArg 430                   450                   470
CTCAAGGAGCCTCCCGAAATAAATCGGCAGATAGGGCCGATGTTCAAAAGGTGGTACAAA
LeuLysGluProProGluIleAsnArgGlnIleGlyProMetPheLysArgTrpTyrLys 490                   510                   530
GAAGAGCTAAAGGGGAAAATAGAAGAGAGGCTTCCAGGCCCTACCAAACCAAAGATTGTG
GluGluLeuLysGlyLysIleGluGluArgLeuProGlyProThrLysProLysIleVal 550                   570                   590
GTAGTATCCCCTGAAAAAAGTAAACCGGAGCAAGCACCCCTTATTGCGGAGAGAGAAGCG
ValValSerProGluLysSerLysProGluGlnAlaProLeuIleAlaGluArgGluAla 610                   630                   650
GGCATCATCATATACACGGGATCGGATGAAGCTTTGAAAGATGCCGCCAAGGAAAACCTG
GlyIleIleIleTyrThrGlySerAspGluAlaLeuLysAspAlaAlaLysGluAsnLeu 670                   690                   710
GGCCTTGGCGAGGAAGCAGAACTAGGCACCAAGGGCGTAGATTTCTACGTGGTCATCCGG
GlyLeuGlyGluGluAlaGluLeuGlyThrLysGlyValAspPheTyrValValIleArg 730                   750                   770
CGTAGCCCTGAAGAGACATGGCACCTAACAGGAGAAGTGAAGTTTCAATCCGACTTTGGC
ArgSerProGluGluThrTrpHisLeuThrGlyGluValLysPheGlnSerAspPheGly
```

FIG. 2B

```
          790                  810                  830
           .                    .                    .
GGAAACCAAGACAACCAGAAACTAGTAGCAAAGGCTTCCATAAGGTTGGACCTTGAGAAG
GlyAsnGlnAspAsnGlnLysLeuValAlaLysAlaSerIleArgLeuAspLeuGluLys 850                  870                  890
           .                    .                    .
AGGCACATAGGAATAGTGGTGGTGGACGGAATGCCTGTGGTGAGCAAGTTTCGTGGGTGG
ArgHisIleGlyIleValValValAspGlyMetProValValSerLysPheArgGlyTrp 910                  930                  950
           .                    .                    .
GCCGGACTGGGGAAAGAAACGATCGTTACATCCGTACTCCTCCTTCCAGACCTGATAGCG
AlaGlyLeuGlyLysGluThrIleValThrSerValLeuLeuLeuProAspLeuIleAla 970                  990
           .                    .
GAGCTCTACCAAAAGGGTGAAGAAGCCCTGGGCCTCTAG
GluLeuTyrGlnLysGlyGluGluAlaLeuGlyLeuEnd
```

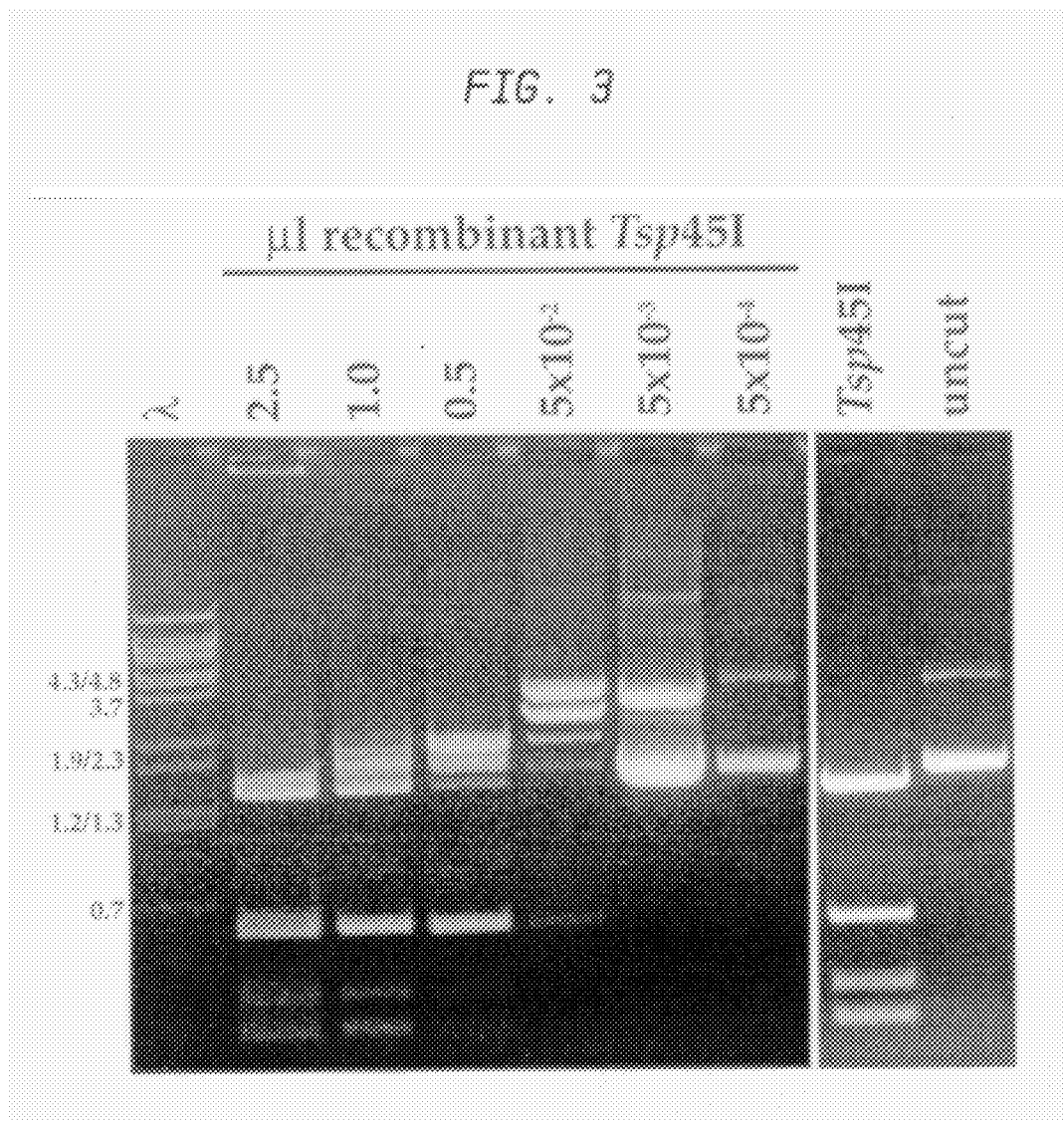

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 1242 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY: Coding Sequence
        ( B ) LOCATION: 1...1239
        ( D ) OTHER INFORMATION:

(x i) SEQUENCE DESCRIPTION: SEQ ID NO:1:

```
ATG AGC CGT AGC TAC CCT GGT TTG ACC CGA AAA GCC CCC TTG AAA GCC      48
Met Ser Arg Ser Tyr Pro Gly Leu Thr Arg Lys Ala Pro Leu Lys Ala
 1               5                  10                  15

TCG AAA ACC TCG GAA CCT TCG CCC TTT AGG TTG GTC TAC CCC GGA AAA      96
Ser Lys Thr Ser Glu Pro Ser Pro Phe Arg Leu Val Tyr Pro Gly Lys
                 20                  25                  30

CGC GAT GAG AAG GAG ATT CTT GAT CAG CCC ACC CCA CAA CTT GTT TTG     144
Arg Asp Glu Lys Glu Ile Leu Asp Gln Pro Thr Pro Gln Leu Val Leu
             35                  40                  45

CGA AAA GAA ACC CTC CTC TTC CTA GGG GGA AAT GCC CCC CTT TTT GAG     192
Arg Lys Glu Thr Leu Leu Phe Leu Gly Gly Asn Ala Pro Leu Phe Glu
         50                  55                  60

ATT GAT CCT ATT GGC ACC TAC TTT TTG GGG GAA AAC GGT CAG GTT CTC     240
Ile Asp Pro Ile Gly Thr Tyr Phe Leu Gly Glu Asn Gly Gln Val Leu
 65                  70                  75                  80

CGG TGG ATG CTC CGG GAG CCT GGT GGG TAT GCG GGG AAG GTC CAG TTG     288
Arg Trp Met Leu Arg Glu Pro Gly Gly Tyr Ala Gly Lys Val Gln Leu
                 85                  90                  95

GTC TAT ATT GAC CCG CCT TAT GGA ACC GGC CAG CAG TTT CTC GTT GGC     336
Val Tyr Ile Asp Pro Pro Tyr Gly Thr Gly Gln Gln Phe Leu Val Gly
                100                 105                 110

GGC GAT GAA ACA GAT CGC GTT GCT ACC GTC AGC CAG CCC AAA AAC GGT     384
Gly Asp Glu Thr Asp Arg Val Ala Thr Val Ser Gln Pro Lys Asn Gly
             115                 120                 125

CAG TTG GGC TAC GAT GAC ACC CTC GAT GGT CCT CAG TTT GTG GAG TTC     432
Gln Leu Gly Tyr Asp Asp Thr Leu Asp Gly Pro Gln Phe Val Glu Phe
         130                 135                 140

CTG AGG GAG CGC TTG ATA CTT CTC AGG GAG CTG ATG GCG GAC TCA GGA     480
Leu Arg Glu Arg Leu Ile Leu Leu Arg Glu Leu Met Ala Asp Ser Gly
145                 150                 155                 160

CTG ATC TTC GTT CAC ATA GAC GAG AAA TAC GGG TTC GAG GTG AAG CTC     528
Leu Ile Phe Val His Ile Asp Glu Lys Tyr Gly Phe Glu Val Lys Leu
                165                 170                 175

ATC CTT GAT GAG GTC TTT GGC CGG CGA AAC TTC GTT AAC CAT ATC GCC     576
Ile Leu Asp Glu Val Phe Gly Arg Arg Asn Phe Val Asn His Ile Ala
                180                 185                 190

CGC ATC GCT TCA AAT CCC AAA AAC TTT TCC CGT AAG GCC TTC GGA TCG     624
Arg Ile Ala Ser Asn Pro Lys Asn Phe Ser Arg Lys Ala Phe Gly Ser
             195                 200                 205

CAA AAG GAC ATG ATC CTC GTC TAC TCC AAA ACG CGG GAC TAC GTT TGG     672
Gln Lys Asp Met Ile Leu Val Tyr Ser Lys Thr Arg Asp Tyr Val Trp
         210                 215                 220

AAC GAA TCG GCT AGC CCC TAT TCG GAA GAG GAG ATC GCT AGG CTT TTC     720
Asn Glu Ser Ala Ser Pro Tyr Ser Glu Glu Glu Ile Ala Arg Leu Phe
225                 230                 235                 240

CCC TTT GTA GAC GAG AAC GGG GAA CGG TAC ACC ACC AAT CCC CTG CAT     768
Pro Phe Val Asp Glu Asn Gly Glu Arg Tyr Thr Thr Asn Pro Leu His
                245                 250                 255

GCT CCT GGA GAA ACC AAG GAT GGC CCT ACC GGA AGG CCT TGG CGA GGA     816
Ala Pro Gly Glu Thr Lys Asp Gly Pro Thr Gly Arg Pro Trp Arg Gly
                260                 265                 270

ATA CTT CCC CCT CCT GGA CGG CAT TGG CGC TAT CCC CCG GAG AAG CTT     864
Ile Leu Pro Pro Pro Gly Arg His Trp Arg Tyr Pro Pro Glu Lys Leu
             275                 280                 285

GAC GAG CTA GAC GCT CAA GGG CTT ATT GTC TGG TCA AAG AAC GGG GTG     912
Asp Glu Leu Asp Ala Gln Gly Leu Ile Val Trp Ser Lys Asn Gly Val
         290                 295                 300

CCG CGG AAG AAA GTT TAC GCT CGG GAT CGC CTG AAG AAG GGG AAG AAG     960
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Pro<br>305 | Arg | Lys | Lys | Val | Tyr<br>310 | Ala | Arg | Asp | Arg<br>315 | Leu | Lys | Lys | Gly | Lys<br>320 | Lys |     |
| CTC<br>Leu | CAG<br>Gln | GAC<br>Asp | GTT<br>Val | TGG<br>Trp<br>325 | CAG<br>Gln | TTC<br>Phe | AAG<br>Lys | GAT<br>Asp | CCT<br>Pro<br>330 | CCG<br>Pro | TAC<br>Tyr | CCG<br>Pro | CGA<br>Arg | TAC<br>Tyr<br>335 | CCC<br>Pro | 1008 |
| ACC<br>Thr | GAG<br>Glu | AAA<br>Lys | AAT<br>Asn<br>340 | CTG<br>Leu | GAC<br>Asp | ATG<br>Met | CTC<br>Leu | AAG<br>Lys<br>345 | CTC<br>Leu | ATC<br>Ile | GTC<br>Val | CAA<br>Gln | ACA<br>Thr<br>350 | GGG<br>Gly | AGT<br>Ser | 1056 |
| AAC<br>Asn | GAG<br>Glu | GGG<br>Gly<br>355 | GAT<br>Asp | TTA<br>Leu | GTG<br>Val | CTC<br>Leu | GAT<br>Asp<br>360 | CCC<br>Pro | TTC<br>Phe | GCA<br>Ala | GGC<br>Gly | TCC<br>Ser<br>365 | GGT<br>Gly | ACT<br>Thr | ACG<br>Thr | 1104 |
| CTT<br>Leu | ATA<br>Ile<br>370 | GCC<br>Ala | TCA<br>Ser | CCC<br>Pro | CTC<br>Leu | TTA<br>Leu<br>375 | AAG<br>Lys | CGG<br>Arg | CGA<br>Arg | TCC<br>Ser | ATC<br>Ile<br>380 | GGC<br>Gly | ATA<br>Ile | GAT<br>Asp | GCC<br>Ala | 1152 |
| TCC<br>Ser<br>385 | TGG<br>Trp | GAG<br>Glu | GCG<br>Ala | GTC<br>Val | AAA<br>Lys<br>390 | GCC<br>Ala | TTC<br>Phe | ACT<br>Thr | AGA<br>Arg | AGG<br>Arg<br>395 | GTG<br>Val | TTA<br>Leu | GAG<br>Glu | GAT<br>Asp | TTC<br>Phe<br>400 | 1200 |
| CCC<br>Pro | AGG<br>Arg | CTA<br>Leu | CAG<br>Gln | CAC<br>His<br>405 | AAG<br>Lys | TTT<br>Phe | GAG<br>Glu | ATT<br>Ile | GTG<br>Val<br>410 | TCC<br>Ser | GCC<br>Ala | TTC<br>Phe | TAG |     |     | 1242 |

( 2 ) INFORMATION FOR SEQ ID NO:2:

( i ) SEQUENCE CHARACTERISTICS:
        ( A ) LENGTH: 413 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

|     |     |     |     |     |     |     |     |     |     |     |     |     |     |     |
|-----|-----|-----|-----|-----|-----|-----|-----|-----|-----|-----|-----|-----|-----|-----|
| Met<br>1 | Ser | Arg | Ser | Tyr<br>5 | Pro | Gly | Leu | Thr | Arg<br>10 | Lys | Ala | Pro | Leu | Lys<br>15 | Ala |
| Ser | Lys | Thr | Ser<br>20 | Glu | Pro | Ser | Pro<br>25 | Phe | Arg | Leu | Val | Tyr<br>30 | Pro | Gly | Lys |
| Arg | Asp | Glu<br>35 | Lys | Glu | Ile | Leu | Asp<br>40 | Gln | Pro | Thr | Pro | Gln<br>45 | Leu | Val | Leu |
| Arg | Lys<br>50 | Glu | Thr | Leu | Leu | Phe<br>55 | Leu | Gly | Gly | Asn | Ala<br>60 | Pro | Leu | Phe | Glu |
| Ile<br>65 | Asp | Pro | Ile | Gly | Thr<br>70 | Tyr | Phe | Leu | Gly | Glu<br>75 | Asn | Gly | Gln | Val | Leu<br>80 |
| Arg | Trp | Met | Leu | Arg<br>85 | Glu | Pro | Gly | Gly | Tyr<br>90 | Ala | Gly | Lys | Val | Gln<br>95 | Leu |
| Val | Tyr | Ile | Asp<br>100 | Pro | Pro | Tyr | Gly | Thr<br>105 | Gly | Gln | Gln | Phe | Leu<br>110 | Val | Gly |
| Gly | Asp | Glu<br>115 | Thr | Asp | Arg | Val | Ala<br>120 | Thr | Val | Ser | Gln | Pro<br>125 | Lys | Asn | Gly |
| Gln | Leu<br>130 | Gly | Tyr | Asp | Asp | Thr<br>135 | Leu | Asp | Gly | Pro | Gln<br>140 | Phe | Val | Glu | Phe |
| Leu<br>145 | Arg | Glu | Arg | Leu | Ile<br>150 | Leu | Leu | Arg | Glu | Leu<br>155 | Met | Ala | Asp | Ser | Gly<br>160 |
| Leu | Ile | Phe | Val | His<br>165 | Ile | Asp | Glu | Lys | Tyr<br>170 | Gly | Phe | Glu | Val | Lys<br>175 | Leu |
| Ile | Leu | Asp | Glu | Val<br>180 | Phe | Gly | Arg | Arg<br>185 | Asn | Phe | Val | Asn | His<br>190 | Ile | Ala |
| Arg | Ile | Ala<br>195 | Ser | Asn | Pro | Lys | Asn<br>200 | Phe | Ser | Arg | Lys | Ala<br>205 | Phe | Gly | Ser |

| | | | | | | | | | | | | | | |
|---|---|---|---|---|---|---|---|---|---|---|---|---|---|---|
| Gln | Lys 210 | Asp | Met | Ile | Leu | Val 215 | Tyr | Ser | Lys | Thr | Arg 220 | Asp | Tyr | Val | Trp |
| Asn 225 | Glu | Ser | Ala | Ser | Pro 230 | Tyr | Ser | Glu | Glu 235 | Ile | Ala | Arg | Leu | Phe 240 |
| Pro | Phe | Val | Asp 245 | Asn | Gly | Glu | Arg | Tyr 250 | Thr | Thr | Asn | Pro | Leu 255 | His |
| Ala | Pro | Gly | Glu 260 | Thr | Lys | Asp | Gly | Pro 265 | Thr | Gly | Arg | Pro 270 | Trp | Arg | Gly |
| Ile | Leu | Pro 275 | Pro | Pro | Gly | Arg | His 280 | Trp | Arg | Tyr | Pro | Pro 285 | Glu | Lys | Leu |
| Asp | Glu 290 | Leu | Asp | Ala | Gln | Gly 295 | Leu | Ile | Val | Trp | Ser 300 | Lys | Asn | Gly | Val |
| Pro 305 | Arg | Lys | Lys | Val | Tyr 310 | Ala | Arg | Asp | Arg | Leu 315 | Lys | Lys | Gly | Lys | Lys 320 |
| Leu | Gln | Asp | Val | Trp 325 | Gln | Phe | Lys | Asp | Pro 330 | Pro | Tyr | Pro | Arg | Tyr 335 | Pro |
| Thr | Glu | Lys | Asn 340 | Leu | Asp | Met | Leu | Lys 345 | Leu | Ile | Val | Gln | Thr 350 | Gly | Ser |
| Asn | Glu | Gly 355 | Asp | Leu | Val | Leu | Asp 360 | Pro | Phe | Ala | Gly | Ser 365 | Gly | Thr | Thr |
| Leu | Ile 370 | Ala | Ser | Pro | Leu | Leu 375 | Lys | Arg | Arg | Ser | Ile 380 | Gly | Ile | Asp | Ala |
| Ser 385 | Trp | Glu | Ala | Val | Lys 390 | Ala | Phe | Thr | Arg | Arg 395 | Val | Leu | Glu | Asp | Phe 400 |
| Pro | Arg | Leu | Gln | His 405 | Lys | Phe | Glu | Ile | Val 410 | Ser | Ala | Phe | | | |

( 2 ) INFORMATION FOR SEQ ID NO:3:

( i ) SEQUENCE CHARACTERISTICS:
        ( A ) LENGTH: 999 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY: Coding Sequence
        ( B ) LOCATION: 1...996
        ( D ) OTHER INFORMATION:

( x i ) SEQUENCE DESCRIPTION: SEQ ID NO:3:

```
ATG  CAA  CAG  ATG  GCC  GAG  TGG  AAC  GTG  TGG  ACA  CAG  AGA  AGC  GTT  GAG        48
Met  Gln  Gln  Met  Ala  Glu  Trp  Asn  Val  Trp  Thr  Gln  Arg  Ser  Val  Glu
 1             5                        10                       15

CTT  CTG  GAG  AAG  GGG  TAT  TTG  GAT  AAA  CTA  CTG  CAG  GTC  TAT  AAA  GGG        96
Leu  Leu  Glu  Lys  Gly  Tyr  Leu  Asp  Lys  Leu  Leu  Gln  Val  Tyr  Lys  Gly
                20                       25                       30

GAA  AGT  GGC  TCT  TCG  AGG  TCA  GTA  CCA  GAG  GAG  GTA  GAG  GAA  AAA  CTT       144
Glu  Ser  Gly  Ser  Ser  Arg  Ser  Val  Pro  Glu  Glu  Val  Glu  Glu  Lys  Leu
           35                       40                       45

CGC  GAG  GCC  TAC  AAG  GCA  TAC  GAG  GGG  AGG  CAG  GAT  AGT  CCG  GAG  GCA       192
Arg  Glu  Ala  Tyr  Lys  Ala  Tyr  Glu  Gly  Arg  Gln  Asp  Ser  Pro  Glu  Ala
      50                       55                       60

GAA  ACG  AAA  CTC  GTG  GAA  GCC  GTG  CTA  AAT  GCC  AGA  AAA  AAG  GTC  GAG       240
Glu  Thr  Lys  Leu  Val  Glu  Ala  Val  Leu  Asn  Ala  Arg  Lys  Lys  Val  Glu
65                       70                       75                       80

CGG  TCC  CCC  TTC  AAT  CAC  CCC  TAC  CTG  CCT  TTG  GTC  TAC  TAC  CTG  GTT       288
Arg  Ser  Pro  Phe  Asn  His  Pro  Tyr  Leu  Pro  Leu  Val  Tyr  Tyr  Leu  Val
```

|  |  |  | 85 |  |  |  |  | 90 |  |  |  |  | 95 |  |  |  |
|---|---|---|---|---|---|---|---|---|---|---|---|---|---|---|---|---|
| TCG | GAA | AAA | GCA | GAA | AAA | GCG | AAC | AAG | GCC | CTT | GAG | GAG | GCA | TTG | CAG | 336 |
| Ser | Glu | Lys | Ala | Glu | Lys | Ala | Asn | Lys | Ala | Leu | Glu | Glu | Ala | Leu | Gln |  |
|  |  | 100 |  |  |  | 105 |  |  |  |  |  | 110 |  |  |  |  |
| GAG | GTT | GCC | TCA | AAG | CAC | CCA | GAA | ACC | ATC | CGC | GTC | CTG | GCC | AAG | GAA | 384 |
| Glu | Val | Ala | Ser | Lys | His | Pro | Glu | Thr | Ile | Arg | Val | Leu | Ala | Lys | Glu |  |
|  |  | 115 |  |  |  |  | 120 |  |  |  |  | 125 |  |  |  |  |
| GCG | CAA | AGA | AGA | GGC | GTA | GAA | GCC | TTG | ATC | CAA | AGG | CTC | AAG | GAG | CCT | 432 |
| Ala | Gln | Arg | Arg | Gly | Val | Glu | Ala | Leu | Ile | Gln | Arg | Leu | Lys | Glu | Pro |  |
|  | 130 |  |  |  |  | 135 |  |  |  |  | 140 |  |  |  |  |  |
| CCC | GAA | ATA | AAT | CGG | CAG | ATA | GGG | CCG | ATG | TTC | AAA | AGG | TGG | TAC | AAA | 480 |
| Pro | Glu | Ile | Asn | Arg | Gln | Ile | Gly | Pro | Met | Phe | Lys | Arg | Trp | Tyr | Lys |  |
| 145 |  |  |  |  | 150 |  |  |  |  | 155 |  |  |  |  | 160 |  |
| GAA | GAG | CTA | AAG | GGG | AAA | ATA | GAA | GAG | AGG | CTT | CCA | GGC | CCT | ACC | AAA | 528 |
| Glu | Glu | Leu | Lys | Gly | Lys | Ile | Glu | Glu | Arg | Leu | Pro | Gly | Pro | Thr | Lys |  |
|  |  |  |  | 165 |  |  |  |  | 170 |  |  |  |  | 175 |  |  |
| CCA | AAG | ATT | GTG | GTA | GTA | TCC | CCT | GAA | AAA | AGT | AAA | CCG | GAG | CAA | GCA | 576 |
| Pro | Lys | Ile | Val | Val | Val | Ser | Pro | Glu | Lys | Ser | Lys | Pro | Glu | Gln | Ala |  |
|  |  |  | 180 |  |  |  |  | 185 |  |  |  |  | 190 |  |  |  |
| CCC | CTT | ATT | GCG | GAG | AGA | GAA | GCG | GGC | ATC | ATC | ATA | TAC | ACG | GGA | TCG | 624 |
| Pro | Leu | Ile | Ala | Glu | Arg | Glu | Ala | Gly | Ile | Ile | Ile | Tyr | Thr | Gly | Ser |  |
|  |  | 195 |  |  |  |  | 200 |  |  |  |  | 205 |  |  |  |  |
| GAT | GAA | GCT | TTG | AAA | GAT | GCC | GCC | AAG | GAA | AAC | CTG | GGC | CTT | GGC | GAG | 672 |
| Asp | Glu | Ala | Leu | Lys | Asp | Ala | Ala | Lys | Glu | Asn | Leu | Gly | Leu | Gly | Glu |  |
|  | 210 |  |  |  |  | 215 |  |  |  |  | 220 |  |  |  |  |  |
| GAA | GCA | GAA | CTA | GGC | ACC | AAG | GGC | GTA | GAT | TTC | TAC | GTG | GTC | ATC | CGG | 720 |
| Glu | Ala | Glu | Leu | Gly | Thr | Lys | Gly | Val | Asp | Phe | Tyr | Val | Val | Ile | Arg |  |
| 225 |  |  |  |  | 230 |  |  |  |  | 235 |  |  |  |  | 240 |  |
| CGT | AGC | CCT | GAA | GAG | ACA | TGG | CAC | CTA | ACA | GGA | GAA | GTG | AAG | TTT | CAA | 768 |
| Arg | Ser | Pro | Glu | Glu | Thr | Trp | His | Leu | Thr | Gly | Glu | Val | Lys | Phe | Gln |  |
|  |  |  |  | 245 |  |  |  |  | 250 |  |  |  |  | 255 |  |  |
| TCC | GAC | TTT | GGC | GGA | AAC | CAA | GAC | AAC | CAG | AAA | CTA | GTA | GCA | AAG | GCT | 816 |
| Ser | Asp | Phe | Gly | Gly | Asn | Gln | Asp | Asn | Gln | Lys | Leu | Val | Ala | Lys | Ala |  |
|  |  |  | 260 |  |  |  |  | 265 |  |  |  |  | 270 |  |  |  |
| TCC | ATA | AGG | TTG | GAC | CTT | GAG | AAG | AGG | CAC | ATA | GGA | ATA | GTG | GTG | GTG | 864 |
| Ser | Ile | Arg | Leu | Asp | Leu | Glu | Lys | Arg | His | Ile | Gly | Ile | Val | Val | Val |  |
|  |  | 275 |  |  |  |  | 280 |  |  |  |  | 285 |  |  |  |  |
| GAC | GGA | ATG | CCT | GTG | GTG | AGC | AAG | TTT | CGT | GGG | TGG | GCC | GGA | CTG | GGG | 912 |
| Asp | Gly | Met | Pro | Val | Val | Ser | Lys | Phe | Arg | Gly | Trp | Ala | Gly | Leu | Gly |  |
|  | 290 |  |  |  |  | 295 |  |  |  |  | 300 |  |  |  |  |  |
| AAA | GAA | ACG | ATC | GTT | ACA | TCC | GTA | CTC | CTC | CTT | CCA | GAC | CTG | ATA | GCG | 960 |
| Lys | Glu | Thr | Ile | Val | Thr | Ser | Val | Leu | Leu | Leu | Pro | Asp | Leu | Ile | Ala |  |
| 305 |  |  |  |  | 310 |  |  |  |  | 315 |  |  |  |  | 320 |  |
| GAG | CTC | TAC | CAA | AAG | GGT | GAA | GAA | GCC | CTG | GGC | CTC | TAG |  |  |  | 999 |
| Glu | Leu | Tyr | Gln | Lys | Gly | Glu | Glu | Ala | Leu | Gly | Leu |  |  |  |  |  |
|  |  |  |  | 325 |  |  |  |  | 330 |  |  |  |  |  |  |  |

( 2 ) INFORMATION FOR SEQ ID NO:4:

( i ) SEQUENCE CHARACTERISTICS:
        ( A ) LENGTH: 332 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:4:

| Met | Gln | Gln | Met | Ala | Glu | Trp | Asn | Val | Trp | Thr | Gln | Arg | Ser | Val | Glu |
|---|---|---|---|---|---|---|---|---|---|---|---|---|---|---|---|
| 1 |  |  |  | 5 |  |  |  |  | 10 |  |  |  |  | 15 |  |

```
Leu Leu Glu Lys Gly Tyr Leu Asp Lys Leu Leu Gln Val Tyr Lys Gly
         20              25                  30
Glu Ser Gly Ser Ser Arg Ser Val Pro Glu Glu Val Glu Glu Lys Leu
         35              40                  45
Arg Glu Ala Tyr Lys Ala Tyr Glu Gly Arg Gln Asp Ser Pro Glu Ala
     50              55                  60
Glu Thr Lys Leu Val Glu Ala Val Leu Asn Ala Arg Lys Lys Val Glu
 65              70                  75                      80
Arg Ser Pro Phe Asn His Pro Tyr Leu Pro Leu Val Tyr Tyr Leu Val
                 85              90                      95
Ser Glu Lys Ala Glu Lys Ala Asn Lys Ala Leu Glu Glu Ala Leu Gln
             100             105                 110
Glu Val Ala Ser Lys His Pro Glu Thr Ile Arg Val Leu Ala Lys Glu
             115             120                 125
Ala Gln Arg Arg Gly Val Glu Ala Leu Ile Gln Arg Leu Lys Glu Pro
         130             135                 140
Pro Glu Ile Asn Arg Gln Ile Gly Pro Met Phe Lys Arg Trp Tyr Lys
145             150                 155                     160
Glu Glu Leu Lys Gly Lys Ile Glu Glu Arg Leu Pro Gly Pro Thr Lys
                165                 170                 175
Pro Lys Ile Val Val Val Ser Pro Glu Lys Ser Lys Pro Glu Gln Ala
             180                 185                 190
Pro Leu Ile Ala Glu Arg Glu Ala Gly Ile Ile Ile Tyr Thr Gly Ser
         195                 200                 205
Asp Glu Ala Leu Lys Asp Ala Ala Lys Glu Asn Leu Gly Leu Gly Glu
     210                 215                 220
Glu Ala Glu Leu Gly Thr Lys Gly Val Asp Phe Tyr Val Val Ile Arg
225                 230                 235                 240
Arg Ser Pro Glu Glu Thr Trp His Leu Thr Gly Glu Val Lys Phe Gln
                245                 250                 255
Ser Asp Phe Gly Gly Asn Gln Asp Asn Gln Lys Leu Val Ala Lys Ala
             260                 265                 270
Ser Ile Arg Leu Asp Leu Glu Lys Arg His Ile Gly Ile Val Val Val
         275                 280                 285
Asp Gly Met Pro Val Val Ser Lys Phe Arg Gly Trp Ala Gly Leu Gly
     290                 295                 300
Lys Glu Thr Ile Val Thr Ser Val Leu Leu Leu Pro Asp Leu Ile Ala
305                 310                 315                 320
Glu Leu Tyr Gln Lys Gly Glu Glu Ala Leu Gly Leu
                325                 330
```

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:5:

GGTTCCATAA GGCGGGTCAA TATAG    25

( 2 ) INFORMATION FOR SEQ ID NO:6:

( i ) SEQUENCE CHARACTERISTICS:
        ( A ) LENGTH: 25 base pairs (B) TYPE: nucleic acid
(C) STRANDEDNESS: single
(D) TOPOLOGY: linear (i i) MOLECULE TYPE: Synthetic DNA (x i) SEQUENCE DESCRIPTION: SEQ ID NO:6:

CTATATTGAC CCGCCTTATG GAACC 25

(2) INFORMATION FOR SEQ ID NO:7:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: Synthetic DNA (x i) SEQUENCE DESCRIPTION: SEQ ID NO:7:

GTGGGGTGGG CTGATCAAGA ATCTCCT 27

(2) INFORMATION FOR SEQ ID NO:8:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: Synthetic DNA (x i) SEQUENCE DESCRIPTION: SEQ ID NO:8:

AGGAGATTCT TGATCAGCCC ACCCCAC 27

(2) INFORMATION FOR SEQ ID NO:9:

(i) SEQUENCE CHARACTERISTICS:
(A) LENGTH: 26 base pairs
(B) TYPE: nucleic acid
(C) STRANDEDNESS: single
(D) TOPOLOGY: linear (i i) MOLECULE TYPE: Synthetic DNA (x i) SEQUENCE DESCRIPTION: SEQ ID NO:9:

TCACCCACAA CCCTCACGCA CTCCAA 26

(2) INFORMATION FOR SEQ ID NO:10:

(i) SEQUENCE CHARACTERISTICS:
(A) LENGTH: 26 base pairs
(B) TYPE: nucleic acid
(C) STRANDEDNESS: single
(D) TOPOLOGY: linear (i i) MOLECULE TYPE: Synthetic DNA (x i) SEQUENCE DESCRIPTION: SEQ ID NO:10:

TTGGAGTGCG TGAGGGTTGT GGGTGA 26

(2) INFORMATION FOR SEQ ID NO:11:

(i) SEQUENCE CHARACTERISTICS:
(A) LENGTH: 26 base pairs
(B) TYPE: nucleic acid
(C) STRANDEDNESS: single
(D) TOPOLOGY: linear (i i) MOLECULE TYPE: Synthetic DNA ( x i ) SEQUENCE DESCRIPTION: SEQ ID NO:11:

AGATGTAGTC GTCCAGGGTG AGCCTG    26

( 2 ) INFORMATION FOR SEQ ID NO:12:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: Synthetic DNA ( x i ) SEQUENCE DESCRIPTION: SEQ ID NO:12:

CAGGCTCACC CTGGACGACT ACATCT    26

( 2 ) INFORMATION FOR SEQ ID NO:13:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: Synthetic DNA ( x i ) SEQUENCE DESCRIPTION: SEQ ID NO:13:

TTGGTATGTA AAGCCCTTCG CGAGG    25

( 2 ) INFORMATION FOR SEQ ID NO:14:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: Synthetic DNA ( x i ) SEQUENCE DESCRIPTION: SEQ ID NO:14:

CCTCGCGAAG GGCTTTACAT ACCAA    25

( 2 ) INFORMATION FOR SEQ ID NO:15:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: Synthetic DNA ( x i ) SEQUENCE DESCRIPTION: SEQ ID NO:15:

TAGTGGCATC GGTGTTGTCG TGGGT    25

( 2 ) INFORMATION FOR SEQ ID NO:16:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: Synthetic DNA ( x i ) SEQUENCE DESCRIPTION: SEQ ID NO:16:

ACCCACGACA ACACCGATGC CACTA    25

( 2 ) INFORMATION FOR SEQ ID NO:17:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:17:

GGACGCGTCG ACGGAGGTTT AAATAATGAG CCGTAGCTAC CCTGGTTTG    49

( 2 ) INFORMATION FOR SEQ ID NO:18:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:18:

GGACGCGTCG ACTCTAGAAG GCGGACACAA TCTC    34

( 2 ) INFORMATION FOR SEQ ID NO:19:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:19:

CTAGTCTAGA GGAGGTTTAA ATAATGCAAC AGATGGCCGA GTGGAAC    47

( 2 ) INFORMATION FOR SEQ ID NO:20:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:20:

CTAGTCTAGA GGAGGTTTAA ATAATGGCCG AGTGGAACGT GTGGACA    47

( 2 ) INFORMATION FOR SEQ ID NO:21:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Synthetic DNA ( x i ) SEQUENCE DESCRIPTION: SEQ ID NO:21:

CGCGGATCCT ATTTAACTAG AGGCCCAGGG CTTCTTCACC    40

( 2 ) INFORMATION FOR SEQ ID NO:22:

( i ) SEQUENCE CHARACTERISTICS:
        ( A ) LENGTH: 47 base pairs (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:22:

CTAGGGATCC GGAGGTTTAA ATAATGCAAC AGATGGCCGA GTGGAAC    47

(2) INFORMATION FOR SEQ ID NO:23:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:23:

CTAGGGATCC GGAGGTTTAA ATAATGGCCG AGTGGAACGT GTGGACA    47

(2) INFORMATION FOR SEQ ID NO:24:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:24:

CGCGGATCCT ATTTAACTAG AGGCCCAGGG CTTCTTCACC    40

METHOD FOR CLONING AND PRODUCING THE TSP45I RESTRICTION ENDONUCLEASE IN E. COLI

BACKGROUND OF THE INVENTION

The present invention relates to cloned DNA encoding the Tsp45I restriction endonuclease (Tsp45I) as well as the Tsp45I modification methylase (M. Tsp45I), and the production of recombinant Tsp45I.

Many species of bacteria contain small circular extrachromosomal genetic elements, known as plasmids. Plasmids have been found in a number of bacteria which live in extreme environments, including the thermophiles, which live at high (>55° C.) temperatures (Munster et al., *Appl. Environ. Microbiol.* 50:1325–1327 (1985); Kristjansson and Stetter, in 'Thermophilic Bacteria', Kristjansson, ed., p. 1–18 (1992)). However, most thermophile plasmids remain 'cryptic' in that functional genes have not been isolated from them, hence leaving their functional significance speculative (Hishinuma et al., *J. Gen. Microbiol.* 104:193–199 (1978); Eberhard et al., *Plasmid* 6:1–6 (1981); Vásquez et al., *FEBS Lett.* 158:339–342 (1983)). Common genes found in other plasmids include those encoding plasmid replication and cellular maintenance, antibiotic resistance, bacteriocin production, sex determination, and other cellular functions (Kornberg and Baker, 'DNA Replication', $2^{nd}$ ed. (1991)). Of particular interest to molecular biologists are plasmids that harbor restriction-modification (R-M) systems.

R-M systems occur naturally in most bacteria, including thermophiles (Hjörleifsdóttir et al., *Biotech. Tech.* 10:13–18 (1996)). The common type II R-M system consists of two genes encoding a restriction endonuclease and its cognate modification methylase (Roberts and Halford, in 'Nucleases', $_2$nd ed., Linn et al., ed.'s, p. 35–88 (1993)). When purified from other bacterial components, restriction endonucleases can be used in the laboratory to cleave DNA molecules into precise fragments for molecular cloning and gene characterization. Thermophilic restriction endonucleases tend to retain their thermophilic character, acting with maximum efficiency at the elevated temperatures of their host strain (Hjörleifsóttir et al., *Biotech. Tech.* 10:13–18 (1996)). Thermophilic enzymes are also more stable than lower-temperature counterparts, being more resistant to both thermal and chemically induced denaturation (Kristjansson, *Trends. Biotech.* 7:349–353 (1989); Coolbear et al., *Adv. Biochem. Eng. Biotech.* 45:57–98 (1992); Cowan, *Biochem. Soc. Symp.* 58:149–169 (1992)). They are therefore invaluable in methodology, such as PCR, in which high temperatures cannot be avoided.

Restriction endonucleases recognize and bind particular sequences of nucleotides (the 'recognition sequence') along the DNA molecule. Once bound, they cleave the molecule within or to one side of the recognition sequence. Over two hundred and thirty two restriction endonucleases with unique specificity have been identified in bacterial species to date. Only about thirty of the over two thousand eight hundred known restriction endonucleases are known to be plasmid-borne (Roberts and Macelis, *Nucl. Acids Res.* 25:248–262, (1997)).

Restriction endonucleases are typically named according to the bacteria from which they are derived (Smith and Nathans, *J. Mol. Biol.* 81:419–423 (1973)). Thus, the *Thermus species* YS45 possesses one known endonuclease activity called Tsp45I (Raven et al., *Nucl. Acids Res.* 21:4397 (1993)). This enzyme recognizes two unique double-stranded DNA sequences: 5'-GTGAC-3' and 5'-GTCAG-3' (which can be conveniently written as 5'-GTSAC-3'). It cleaves the DNA before the first G in this site (along both strands) leaving four nucleotides as single stranded 5' overhangs at each end of the cleaved DNA. The enzyme has maximal activity at about 65°, a temperature at which YS45 grows well.

It is commonly accepted that restriction endonucleases evolved to play a protective role in the welfare of the bacterial cell (Wilson and Murray, *Annu. Rev. Genet.* 25:585–627 (1991)). They impart bacteria with resistance to infection by foreign viral or plasmid DNA, which might otherwise destroy or parasitize them. Invading foreign DNA is cleaved at recognition sites by the bacterial endonuclease, disabling many infecting genes and/or rendering the foreign DNA susceptible to further degradation by non-specific nucleases.

The other component of type II bacterial R-M systems is the modification methylase (Roberts and Halford, in 'Nucleases', $_2$nd ed., Linn et al., ed.'s, p. 35–88 (1993)). Modification methylases provide the means by which bacteria are able to protect and distinguish their own DNA from foreign DNA. They recognize and bind to the same recognition sequence as their corresponding restriction endonuclease. For example, the methylase recognizing 5'-GTSAC-3' is known as M. Tsp45I. Modification methylases do not cleave DNA, but rather chemically modify one particular nucleotide within the recognition sequence by the addition of a methyl group. Following methylation, this sequence is no longer cleaved by the corresponding endonuclease. The DNA of a bacterial cell is always fully modified by virtue of the activity of its modification methylase. It is therefore completely insensitive to the presence of the endogenous restriction endonuclease. It is only unmodified and therefore identifiably foreign DNA that is sensitive to restriction endonuclease recognition and cleavage.

It is often particularly difficult to cultivate thermophilic bacteria within the laboratory. They require high temperatures and often-unknown environmental conditions for acceptable growth (Kristjansson and Stetter, in 'Thermophilic Bacteria', Kristjansson, ed., p. 1–18 (1992)). However, with the advent of genetic engineering, it is now possible to clone genes from thermophiles into more easily cultivatable laboratory organisms, such as *E. coli* (Kristjansson, *Trends Biotech.* 7:349–353 (1989); Coolbear et al., *Adv. Biochem. Eng. Biotech.* 45:57–98 (1992)). The expression of such genes can be finely controlled within *E. coli*.

A number of methods for isolating R-M systems from diverse bacteria have been devised. The earliest cloning efforts relied upon bacteriophage infection as a means of identifying or selecting restriction endonuclease clones (EcoRII: Kosykh et al., *Molec. Gen. Genet.* 178: 717–719, (1980); HhaII: Mann et al., *Gene* 3: 97–112, (1978); PstI: Walder et al., *Proc. Nat. Acad. Sci.* 78:1503–1507, (1981)). Cells that carry cloned R-M genes can, in principle, be selectively isolated as survivors from libraries that have been exposed to phage. This method is of limited value, as many cloned R-M genes do not manifest sufficient phage resistance to confer selective survival. The likelihood of cloning a Thermus R-M system by this method is further reduced, as only one Thermus phage (fYS40) has been described (Sakaki and Oshima, *J. Virol.* 15:1449–1453, (1975)).

R-M systems have also been cloned by selection for an active methylase ('methylase-selection' (Kiss et al., *Nucl. Acids Res.* 13: 6403–6421, (1985)), or endonuclease ('endo-blue method', (Fomenkov et al., *Nucl. Acids Res.*

22:2399–2403, (1994)). These methodologies rely upon the expression of said genes in *E. coli* by their introduced promoters. Thermus promoters can significantly diverge from those of *E. coli* (Maseda and Hoshino, *FEMS Microbiol. Lett.* 128:127–134, (1995)), and may not function at all (Wayne and Xu, Gene (in press), (1997)). It is therefore difficult to predict whether such methodology can be used to clone a Thermus R-M system.

A few plasmid-borne R-M systems have been characterized in diverse bacterial species prior to transfer to *E. coli* (EcoRV, Bougueleret et al., *Nucl. Acids Res.* 12:3659–3676 (1984); PaeR7: Gingeras and Brooks, Proc. Nat. Acad. Sci. USA 80:402–406, (1983); Theriault and Roy, Gene 19:355–359 (1982); PvuII: Blumenthal et al., *J. Bacteriol.* 164:501–509 (1985)). However, no eubacterial, and only one archaeon (MthTI, Nolling and DEVOS, *J. Bacteriol.* 17:5719–5726 (1992)) thermophilic plasmid-borne R-M system has been previously expressed in *E. coli*. The cloning of thermostable proteins, such as restriction endonucleases, has been hampered by the lack of molecular methodologies within thermophiles. It is often simpler to clone said genes into *E. coli* prior to functional characterization (Kirino et al., *Eur. J. Biochem.* 220:275–281 (1994); Moriyama et al., *J. Biochem.* 117:408–413 (1995); Numata et al., *Prot. Eng.* 8:39–43 (1995)).

The purification of recombinant proteins from *E. coli* has also been better established than that from thermophiles.

Therefore, the production of recombinant proteins is often simpler and produces larger yields than those obtained through conventional purification from the original thermophile (Kristjansson, *Trends Biotech.* 7:349–353 (1989); Coolbear et al., *Adv. Biochem. Eng. Biotech.* 45:57–98 (1992); Ishida and Oshima, *J. Bacteriol.* 176:2767–2770 (1994)). There is commercial incentive to produce thermostable endonucleases which are usually more stable to heat and denaturing conditions then mesophilic (grow between 20° and 50° C.) counterparts (Wiegel and Ljungdahl, *CRC Crit. Rev. Biotech.* 3:39–108); Kristjansson, Trends Biotech. 7:349–353 (1989); Coolbear et al., *Adv. Biochem. Eng. Biotech.* 45:57–98 (1992)). These thermostable enzymes can also be used in a variety of assays, such as PCR, in which high temperatures cannot be 'avoided. The plasmids of thermophiles are therefore an appropriate source for finding thermophilic R-M systems.

SUMMARY OF THE INVENTION

The present invention relates to recombinant DNA molecules encoding the Tsp45I gene (tsp45IR), and the cognate M. Tsp45I gene (tsp45IM), from *Thermus species* YS45 introduced into *E coli*.

The Tsp45I R-M system could in principle be cloned by several methods including: phage selection; the 'endo-blue method';'methylase-selection'; or plasmid sub-cloning. There are no known phage which infect *Thermus species* YS45. Selection cloning requires that Thermus strain YS45 promoters and RBS function strongly within *E. coli*. In addition, most cloning vectors contain multiple Tsp45I sites (9 in pBR322, 4 in pUC19). The introduced M.Tsp45I promoter may not express enough M. Tsp45I to modify all the Tsp45I sites of its cloning vector. It is therefore unlikely that the above-noted selective methods would isolate the Tsp45I R-M system. The production of these selective libraries often begins with 'genomic DNA preparation' as well. In a pure genomic preparation, plasmid-derived DNA will be excluded. As the Tsp45I R-M system is plasmid-derived (see below), it is probable that only plasmid sub-cloning can be used for its isolation.

There has been great interest in establishing systems that allow for genetic transfer between diverse bacterial species. A few plasmid vectors that can be transferred between mesophiles and thermophiles have been previously constructed (Koyoma et al., *FEMS Microbiol. Lett.* 72:97–102 (1990); Lasa et al., *J. Bacteriol.* 174:6424–6431 (1992); Raven, in '*Thermus species*', Sharp and Williams, ed.'s, p.157–184 (1995)). These so-called 'shuttle-vectors' allow for the transfer of genes between environments of different temperatures. Using these vectors, theoretically a gene can be mutated within a mesophile, transferred to a thermophile, and then its encoded protein selected for increased thermostability. In this way, mesophile-thermophile shuttle-vectors can be used to conduct directed evolution, or protein engineering, on desirable genes.

Mesophile-thermophile shuttle vectors require origins of replication (oris) to be genetically maintained and transferred within each bacterial species. To construct appropriate mesophile-thermophile shuttle-vectors we chose to introduce randomly digested thermophile plasmid DNA into the mesophilic vector pUC19. Plasmid pUC19 uses the ColEI ori to replicate within the mesophile *E. coli,* and does not replicate within the plasmid accepting (transformable) thermophile *Thermus thermophilus* HB8 (Koyama et al., *J. Bacteriol.* 166:338–340 (1986)). We reasoned that the introduction of plasmid DNA from related *Thermus species*, which contained a complete thermophilic ori, would confer plasmid replication within HB8.

The thermophilic eubacterium *Thermus species* YS45 (Raven et al., *Nucl. Acids Res.* 21:4397 (1993)) contains two cryptic plasmids, and grows between 55° and 70° C. We randomly digested these plasmids with a variety of restriction endonucleases to produce fragments that could be cloned into pUC1 9-derived vectors. A pUC19-derived plasmid with a 4.2-kb XbaI fragment of the small plasmid (pTsp45s, 5.8 kb) of YS45 replicated within HB8. Therefore this XbaI fragment must contain a thermophilic ori. Subsequent analysis revealed that only 2.3 kb (an NheI fragment) within the 4.2 kb was necessary for thermophilic plasmid replication, and that it encoded a replication protein (RepT). Two sequences matching DnaA boxes, involved in other DNA replicative systems (Kornberg and Baker, 'DNA Replication', $_2$nd ed. (1992)) were also found in this 2.3-kb ori (Wayne and Xu, Gene (in press) (1997)).

In the course of sequencing the 4.2-kb XbaI ori fragment of pTsp45s, another significant open reading frame (ORF) was found. This ORF of 1242 nt, beginning with ATG (start codon) and ending with TAG (stop codon), could encode a 413 aa protein with predicted MW of 47.0 kDa. BLAST and FastA computer searches showed that this putative protein has strong homology (50% similarity, 40% identity) with M.EcaI (Brenner et al., *Nucl. Acids Res.* 18:355–359 (1990)), which recognizes 5'-GGTNACC-3' (where N can be any nt). Since Tsp45I recognizes the inner 5 bp of this sequence (GTSAC) we predicted that we had cloned the M. Tsp45I gene (tsp45IM).

Other homologous methylases with similar recognition sequences have been previously reported (M.BsuFI-M.MspI, M.BsuBI-M.PstI, M.TaqI-M.TthHB81, M.Cfr9I-M.XmaI, M.Cfr9I-M.SmaI, and M.FnuDI-M.NgoPI-M.NgoPII)(Wilson and Murray, *Annu. Rev. Genet.* 25:585–627 (1991)).

We cloned the predicted tsp45IM via PCR into pACYC184 for expression in *E. coli*. Primers with an appropriately spaced ribosome-binding site (RBS) were constructed to precede tsp45IM. PCR was conducted using a plasmid containing the 4.2-kb XbaI fragment of pTsp45s. The pACYC184-tsp45IM vector contains seven Tsp45I recognition sites. Plasmid DNA from pACYC184-tsp45IM transformants was digested with Tsp45I (produced directly from YS45 cells, New England Biolabs, Inc., Beverly, Mass.). The pACYC184-tsp45IM plasmids (properly oriented for M. Tsp45I expression) were not cut by Tsp45I, indicating that the cloned M. Tsp45I had pre-modified (methylated) the pACYC184 DNA.

Since most genes of type II R-M systems occur in close proximity to each other (Wilson, *Nucl. Acids Res.* 19:2539–2566 (1991)), we postulated that Tsp45I was encoded by another ORF on pTsp45s. We also found that the remaining 1.6 kb XbaI fragment of pTsp45s could not be cloned into pUC19, possibly indicating toxicity of an endonuclease within it. Restriction mapping showed that the 1.6 kb could be subdivided into two XbaI-PstI fragments of 0.9 and 0.7 kb. These were cloned and sequenced in pUC19 with their positions, with respect to pTsp45s, determined by mapping analysis. A significant ORF was found directly upstream of tsp45IM. The PstI digestion cut within the ORF, presumably destroying the gene and removing the toxic effect.

The predicted tsp45IR directly upstream of tsp45IM is 999 or 990 nt encoding 332 or 329 aa. There are two possible start (ATG) codons at the beginning of this ORF accounting for the two possible sizes. The ORF would generate a protein with predicted MW of either 37.4 or 37.0 kDa. BLAST and FastA computer searches with this ORF revealed no significant homologies with other known proteins or with M. Tsp45I. This uniqueness is also typical of restriction endonucleases (Wilson and Murray, *Annu. Rev. Genet* 25:585–627 (1991)). The predicted tsp45IR and tsp45IM converge (oppose transcriptionally) to a XbaI site in pTsp45s, overlapping by four bp. Their stop codons (TAG) are within this XbaI (5'-TCTAGA-3') site.

We chose to clone tsp45IR (both 990 nt and 999 nt possibilities, separately) via PCR into pET21a (Novagen, Inc., (Madison, Wis.) T7 promoter, lac operator). Primers were constructed to precede the ORF with an appropriately spaced RBS. PCR was carried out on plasmid DNA prepared directly from YS45 cells. *E. coli* cells protected by the pACYC184-tsp45IM plasmid were transformed with pET21a-tsp45IR. A few clones were found to contain both plasmids, and following IPTG-induction, crude cell extracts were prepared from these to examine recombinant Tsp45I activity in vitro. Plasmid pUC19 with four Tsp45I sites was digested with the crude cell extracts at 65° C. Two extracts (one from a 999-nt clone, the other from a 990-nt clone) showed a digestion pattern matching that of Tsp45I produced from YS45. This indicated that both tsp45IR and tsp45IM had been cloned.

However, pACYC184-tsp45IM, and pET21 a-tsp45IR were not stably maintained in *E. coli*. Sub-cultures did not maintain the pET21 a-tsp45IR plasmid, and so Tsp45I activity was quickly lost. This is probably due to incomplete protection of the *E coli* chromosome by the M. Tsp45I. A delicate balance between expression of each component of the R-M system must exist to generate a stable cell line. The copy-number of each plasmid, and the activity of each genes' promoter affect this balance. It is difficult to predict which vectors will produce the greatest stability. In this case, a relatively strong T7 promoter in the moderate-copy number pET21 a-tsp45IR is toxic to cells containing the low-copy number pACYC184-tsp45IM utilizing a weaker tetracycline resistance promoter.

To generate a stable clone which produced recombinant Tsp45I we re-cloned tsp45IM and tsp45IR in different vectors via PCR. Plasmids were produced as pBR322-tsp45IM (moderate copy-number, weak tetracycline resistance promoter) and pACYC184-T7-(+/−ter)-tsp45IR (low copy number, strong T7 promoter with inducible lac operator from pET11a (Novagen, Inc., Madison, Wis.), with or without four transcription terminators (ter)). The TER sequences from rrnB (Kong et al., *J. Biol. Chem.* 268:1965–1975 (1993)) precede the T7 promoter in pACYC184-T7ter to prevent upstream transcriptional readthrough to the introduced gene. PCR primers used appropriately spaced preceding RBS's to assure proper translation. Several *E. coli* clones (with both forms of tsp45IR in vectors with or without ter) maintained both plasmids for numerous generations. When crude cell extracts were produced from these IPTG-induced clones they contained high levels of Tsp45I activity.

The Tsp45I R-M system is plasmid-borne within its thermophilic host. Interestingly, no obvious Thermus promoters are found upstream of its genes. It is therefore unlikely to have been cloned by any method relying upon expression using a native promoter in *E. coli*. The genes (tsp45IM and tsp45IR) converge and overlap by four bp on a small natural plasmid (pTsp45s, 5.8 kb) of *Thermus species* YS45. The genes can be stably expressed in *E. coli*, and recombinant Tsp45I produced. We estimate that our clones produce $3\times10^5$ units of recombinant Tsp45I per gram of wet cells. This is about a ten-fold increase over that prepared from native host YS45 (New England Biolabs, Inc., Beverly, Mass., unpublished observations).

BRIEF DESCRIPTION OF THE FIGURES

FIG. 1 is the DNA sequence (SEQ ID NO:1) of the M. Tsp45I gene (tsp45IM) and its encoded amino acid sequence (SEQ ID NO:2).

FIG. 2 is the DNA sequence (SEQ ID NO:3) of the Tsp45I gene (tsp45IR) and its encoded amino acid sequence (SEQ ID NO:4) with two possible start codons.

FIG. 3 is the Tsp45I activity assay using recombinant cell extracts on pUC19 plasmid DNA; native enzyme control digestion of pUC19; and BstEII-digested phage lambda (X) size markers.

DETAILED DESCRIPTION OF THE INVENTION

Figure 4:
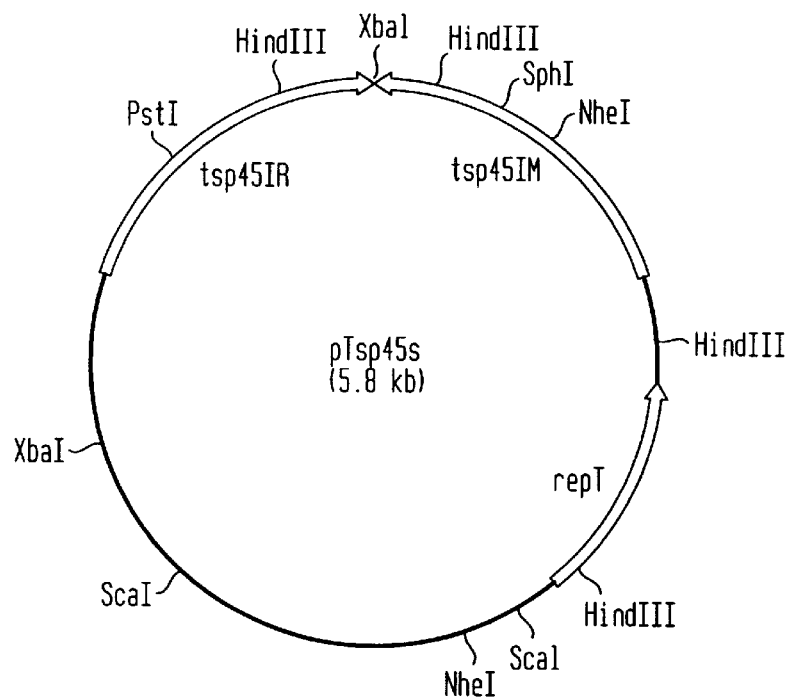
FIG. 4 is the genetic organization of the Tsp45I R-M system within plasmid pTsp45s of *Thermus species* YS45.
Figure 5:
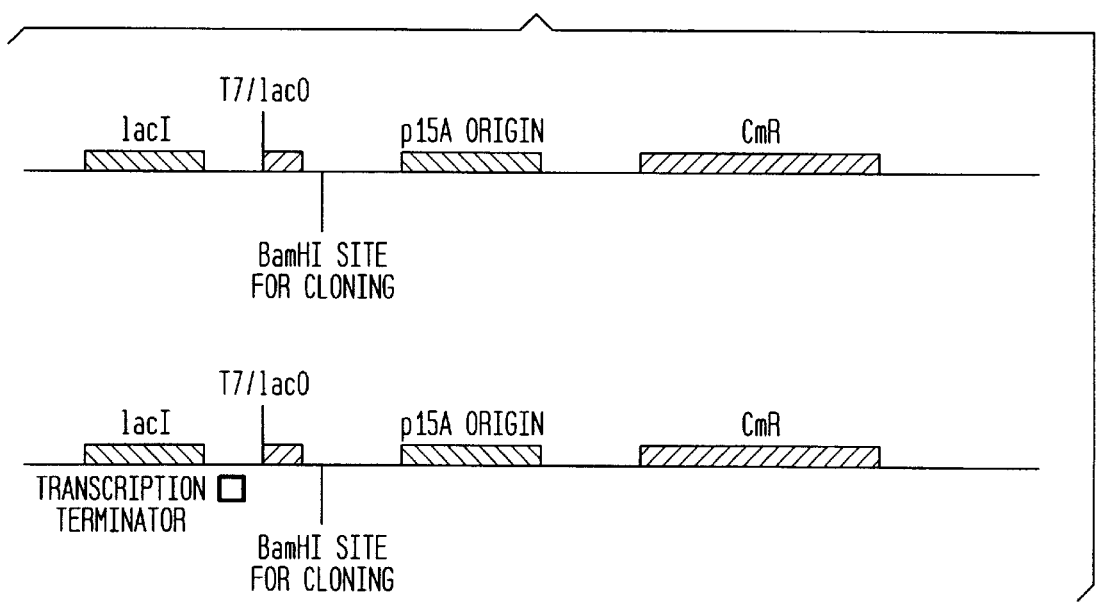
FIG. 5 is the schematic diagram of pACYC184-T7 and pACYC184-T7ter

The method described herein by which the Tsp45I restriction endonuclease and its cognate methylase gene are preferably cloned and expressed using the following steps:

1. The plasmid DNA of *Thermus species* YS45 is purified.

2. The DNA is digested with a series of restriction endonucleases to generate <2-kb fragments, some of which contain the entire tsp45IM. The digestion pattern also generates a plasmid 'map'. This map is used to orient and localize genes within the plasmid.

3. The digested plasmid DNA is then ligated into similarly cleaved/CIP treated pUC19 (ampicillin resistant) cloning vectors. The ligated DNA is used to transform an appropriate host, i.e. a HsdR-, McrBC-, Mrr strain, such as *E. coli* strain RR1. The DNA/cell mixtures are then plated on ampicillin selective media to grow only transformed cells.

4. Individual transformed colonies are grown in ampicillin selective media overnight to amplify the individual plasmids that they contain. The recombinant plasmids are purified and digested in vitro with a variety of endonucleases to map their introduced DNA, and to identify overlapping or redundant clones. The recombinant map is assembled, and then compared with that of the original thermophilic plasmids.

5. The inserted DNA of the recombinant pUC19 clones is sequenced. To facilitate sequencing of large inserts (>1 kb), they are further sub-cloned within pUC19 based upon their preliminary sequence and mapping. The sequenced DNA is then assembled to match that of the thermophilic plasmid map. In this way a cryptic thermophilic plasmid (pTsp45s) is completely sequenced within *E. coli*. ORFs within sequenced pTsp45s are compared with known sequences of modification methylases using BLAST and FastA computer programs. An ORF, encoding 413 aa, with strong homology to other modification methylases is likely M.Tsp45I.

6. Once the likely methylase gene is defined, it is amplified by PCR from the original thermophilic plasmid or an appropriate pUC19 clone. The amplified gene is cloned and expressed within a vector utilizing a tetracycline resistance promoter (pACYC184 or pBR322) within *E. coli*. Plasmids pACYC184 and pBR322 contain seven and nine Tsp45I recognition sites, respectively. The encoded M. Tsp45I modifies all DNA within the cell, including the introduced plasmid. Plasmid DNA isolated from transformants expressing M. Tsp45I is resistant to digestion with Tsp45I.

7. Since type II R-M system genes are found within close proximity, tsp45IR will be located adjacent to tsp45IM in pTsp45s. A large ORF (329 or 332 aa, based on two possible start codons) adjacent to tsp45IM converges and overlaps it by four bp. A fragment containing this ORF cannot be cloned in *E. coli*, suggesting that this toxicity might be due to an endonuclease.

8. The predicted tsp45IR is amplified by PCR from the original thermophilic plasmid DNA. The gene is cloned into IPTG-inducible vectors utilizing the strong T7 promoter and lac operator (pET21a or pACYC184-T7). Tsp45I resistant transformants, which must express M. Tsp45I, are then used as a suitable host for cloning tsp45IR. M. Tsp45I protects these cells from Tsp45I expression. The most stable system contains the pBR322-tsp45IM and pACYC184-T7-tsp45IR plasmids in an *E. coli* ER2566 host (BL21 derivative, fhuA2 endA1, from New England Biolabs, Inc., Beverly, Mass.). Upon IPTG-induction, this strain produces about $3 \times 10^5$ units of recombinant Tsp45I per gram of wet cells.

The following example is given to illustrate embodiments of the present invention, as it is presently preferred to practice. It will be understood that this Example is illustrative, and that the invention is not to be considered as restricted thereto except as indicated in the appended claims.

The references cited above and below are hereby incorporated by reference.

EXAMPLE I

CLONING OF Tsp45I RESTRICTION ENDONUCLEASE GENE

1. Cloning of a plasmid (pTsp45s) native to Thermus species YS45.

*Thermus species* YS45 (Raven et al., *Nucl. Acids Res.* 21:4397 (1993) obtained from R.A.D. Williams of Queen Mary and Westerfield College, University of London) can be grown in modified *Thermus thermophilus* liquid media (Oshima and Imahori, *J. Sys. Bacteriol.* 24:102–112 (1974)) consisting of 0.5% tryptone (Difco Laboratories, Detroit, Mich.), 0.4% yeast extract (Difco Laboratories, Detroit, Mich.), 0.2% NaCl at pH 7.5. Cells are plated in this media with 3% agar. Plated colonies are distinguishable after two days incubation at 55°–70° C. Individual colonies form dense liquid overnight cultures (3–10 ml) at 55°–70° C. in a shaking waterbath. One-ml aliquots of overnight cultures are pelleted and stored at −20° C. for up to one month without loss of viability (J. Berenguer, personal communication). Overnight cultures are also stably maintained in media with 25% glycerol at −70° C.

Ten ml of 70° C. overnight YS45 culture is diluted 1:1000 in 500 ml of Thermus media, and grown overnight at 70° C. to generate plasmid DNA. Plasmid DNA is prepared via the Qiagen mid-prep protocol (Qiagen, Inc., Studio City, Calif.) with the addition of 2 mg lysozyme per ml. Lysis is very inefficient without the presence of lysozyme in the first resuspension buffer (Oshima and Imahori, *J. Sys. Bacteriol.* 24:102–112 (1974)). Routinely, between 50–150 μg of plasmid DNA is obtained from 500 ml of overnight YS45 culture.

YS45 contains two plasmids of 5.8 (pTsp45s) and approximately 12 kb (pTsp45I) (Wayne and Xu, Gene, 195:321–328 (1997)). Each plasmid contains a single PstI site useful for linearizing and visualizing the plasmids on agarose gels. Plasmid pTsp45s also contains two XbaI sites that generate 4.2 and 1.6-kb fragments. This plasmid is extensively mapped and cloned into pUC19 as three fragments: 4.2-kb XbaI-XbaI, 0.7-kb XbaI-PstI, and 0.9-kb PsfI-XbaI. The 4.2-kb fragment is then further mapped and sub-cloned into pUC19 as six smaller fragments: 0.4-kb XbaI-HindIII, 1.1-kb HindIII-HindIII, 0.7-kb HindIII-HindIII, 0.5-kb HindIII-ScaI, 1.0-kb ScaI-ScaI, and 0.5-kb ScaI-XbaI. Cloning was accomplished by isolating digested fragments from agarose gels and combining them with compatibly cut pUC19 by standard methods (Sambrook et al., 'Molecular Cloning A Laboratory Manual', $_2$nd ed. (1989)).

The clones are sequenced using universal and reverse M13/pUC primers (New England Biolabs, Inc., Beverly, Mass.). Preliminary sequencing was used to generate 12 additional primers (synthesized at New England Biolabs, Inc., Beverly, Mass.) to refine and correct sequencing errors. The primers (shown as top and bottom strand pairs) are: 5'-GGTTCCATAAGGCGGGTCAATATAG-3' (SEQ ID NO:5), 5'-CTATATTGACCCGCCTTATGGAACC-3' (SEQ ID NO:6); 5'-GTGGGG TGGGCTGATAAGAATCTCCT-3' (SEQ ID NO:7), 5'-AGGAGATTCTT GATCAGCCCACCCCAC-3' (SEQ ID NO:8); 5'-TCACCCACAACCCTC ACGCACTCCAA-3' (SEQ ID NO:9), 5'-TTGGAGTGCGTGAGGGTTGT GGGTGA-3' (SEQ ID NO:1 0); 5'-AGATGTAGTCGTCCAGGGTGAGCC TG-3' (SEQ ID NO: 11),5'-CAGGCTCACCCTGGACGACTACATCT-3' (SEQ ID NO:12); 5'-TTGGTATGTAAAGCCCTTCGCGAGG-3' (SEQ ID NO:13), 5'-CCTCGCGAAGGGCTTTACATACCAA-3' (SEQ ID NO:14); and 5'-TAGTGGCATCGGTGTTGTCGTGGGT-3' (SEQ ID NO:15), 5'-A CCCACGACAACACCGATGCCACTA-3' (SEQ ID NO:16) (underlined bases are in pTsp45s, but were not originally synthesized in these primers).

2. Cloning and expression of tsp45IM in pACYC184.

The complete sequence of pTsp45s is examined for the presence of coding regions (ORFs) by translating the nucleotide sequence in all six frames. BLAST computer comparisons (Altschul, et al., *J. Molec. Biol.* 215:403–410

(1990)) with known proteins in the GenBank bacterial database reveal high homology between a 413 aa ORF and 1 0 M.EcaI, and other modification methyltransferases. FastA comparisons with the nucleotide sequence reveal similar homologues to its 1242 nt. The ORF is entirely contained within a 4.2-kb fragment derived from pTsp45s. M.EcaI recognizes 5'-GGTNACC-3', whereas Tsp45I recognizes 5'-GTSAC-3'. Other modification methyltransferases with similar recognition sequences show strong homology, so it is predicted that the ORF encodes M. Tsp45I.

To establish that the ORF encodes M. Tsp45I, it is cloned via PCR into vector pACYC184. The gene is amplified from the 4.2-kb insert in pUC19 DNA using primers that flank it with SalI (5'-GTCGAC-3') sites. In addition the forward PCR primer contains an appropriately spaced RBS (5'-GGAGGT-3') for expression of the gene in E. coli (Skoglund et al., Gene 88:1–5 (1990)). The forward (first eight codons) and reverse (final seven codons) primers are, respectively: 5'-GGACGCGTCGACGGAGGTTTAAATAATGAGCC-GTAGCTACCCTG GTTTG-3' (SEQ ID NO:17), and 5'-GGACGCGTCGACTCTAGAAGGCG GACACAATCTC-3' (SEQ ID NO:18).

The PCR reaction is carried out on 10 ng of the 4.2-kb insert within pUC19 (30 cycles of 95° C. for one minute, 60° C. for one minute, 72° C. for one minute) using Vent® DNA polymerase (New England Biolabs, Inc., Beverly, Mass.). The expected approximately 1.3-kb PCR product is extracted and precipitated from the reaction, as it is the sole product when analyzed on agarose gels. The product is digested with SalI overnight, and then ligated to similarly cut/CIP treated pACYC184. The PCR product is inserted within the tetracycline resistance gene of pACYC184.

The ligated DNA is used to transform ER2504 (BL21 derivative, fhuA2endA1, from New England Biolabs, Inc., Beverly, Mass.) cells selected on 30 µg/ml chloramphenicol plates at 37° C. Colonies are streaked on 15 µg/ml tetracycline plates to confirm tetracycline sensitivity (indicating an insert) prior to plasmid analysis. Plasmids are purified from overnight mini-cultures by standard means (Sambrook et al., 'Molecular Cloning A Laboratory Manual', $2^{nd}$ ed. (1989)), and digested with SalI. Plasmids from clones with 1.3-kb SalI inserts are then digested with Tsp45I (at 65° C.) prepared from YS45 (New England Biolabs, Inc., Beverly, Mass.). About 33% of the selected colonies are resistant to Tsp45I digestion, indicating that pACYC184's seven Tsp45I sites are modified by the cloned M.Tsp45I. The properly oriented tsp45IM is expressed via pACYC184's tetracycline resistance promoter, and apparently functions at 37° C. These plasmids are digested by other endonucleases, indicating that the cloned M. Tsp45I has methylated only Tsp45I sites.

3. Cloning of tsp45IR in pET21a, and expression within M.Tsp45I pre-modified E. coli cells.

The sequence analysis of pTsp45s reveals another ORF adjacent and converging upon that of tsp45IM. The ORFs overlap at their TGA stop codons within a XbaI site by four bp. Since type II R-M system genes are found in close proximity, this second ORF probably encodes Tsp45I. The ORF has two possible start codons (ATG) so that it is either 329 or 332 aa (990 or 999 nt). The ORF is entirely contained within a 1.6-kb XbaI fragment of pTsp45s, which cannot be directly cloned in E. coli. This indicates that the ORF is toxic and possibly an endonuclease. The complete ORF sequence is deduced from two smaller sub-clones that divide the 1.6-kb fragment with PstI (0.9 and 0.7 kb). These fragments can be cloned in E. coli, as they do not contain the complete toxic ORF.

Primers are generated to flank the complete ORF with XbaI (5'-TCTAGA-3') and BamHI (5'-GGATCC-3') sites for cloning within the inducible expression vector pET21 a. A preceding appropriately spaced RBS (5'-GGAGGT-3') is also placed in the forward primer to insure efficient expression from pET21 a's T7 promoter. Forward primers are generated for both possible start codons. The forward (first eight codons) and reverse (last eight codons) primers are, respectively: 5'-CTAGTCTAGAGG- AGGTTTAAATAAT-GCAACAGATGGCCGAGTGGA AC-3' (332 aa) (SEQ ID NO:19) or 5'-CTAGTCTAGAGGAGGTTTAA ATAATGGCCGAGTGGAACGTGTGGACA-3' (329 aa) (SEQ ID NO:20), and 5'-CGCGGATCCTATTTAACTAGAGGCCCAGGGCTTCT TCACC-3' (SEQ ID NO:21).

The PCR reaction is carried out on 30 ng of YS45 plasmid DNA (30 cycles of 95° C. for one minute, 60° C. for one minute, and 72° C. for one minute) using Vent® DNA polymerase (New England Biolabs, Inc., Beverly, Mass.). The expected approximately 1.0-kb PCR product is extracted from an agarose gel slice. The gel is digested with β-agarase according to the manufacturer's suggestions (New England Biolabs, Inc, Beverly, Mass.) and then precipitated. The PCR product is digested with BamHI and XbaI for two hours, and then ligated to similarly cut pET21 a. This introduces the PCR product downstream of pET21 a's inducible T7 promoter.

The ligated DNA is then used to transform ER2504 cells harboring pACYC184-tsp45IM. Clones are isolated on 30 µg/ml chloramphenicol and 100 µg/ml ampicillin plates at 30° C. (to reduce un-induced T7 activity). Plasmid DNA is isolated from transformants and visualized on agarose gels for the presence of both pACYCI 84-tsp45IM and pET21a-tsp45IR. In the screening, 13% of transformants contain both plasmids, but only 2.7% do not lose pET21a-tsp45IR upon sub-culture to the next generation. This two-plasmid system is not stable, probably due to incomplete protection of chromosomal DNA by M.Tsp45I, or due to overexpression of Tsp45I. It is difficult to predict what level of plasmid copy-number and promoter expression of an R-M system will be tolerated by E. coli.

However, the few colonies harboring both vectors can be induced to produce recombinant Tsp45I. Overnight cultures are diluted 1:1000 in LB media (30 µg/ml chloramphenicol, 100 µg/ml ampicillin) and grown for three to four hours at 30° C. (exponential phase) prior to induction with 0.25 mM IPTG for an additional two hours at 37° C. Cells from these cultures are sonicated (in 10 mM Tris -Hcl, 10 mM β-mercaptoethanol, pH 8.0) to generate crude cell lysates. Dilutions of these lysates are used to digest 1 µg of pUC19 in vitro (four Tsp45I sites) at 65° C. for one hour. The digested pUC19 is then compared with that digested by Tsp45I produced directly from YS45 cells. One ml of crude lysate from two independent clones (harboring both plasmids, one with 332 aa Tsp45I and the other with 329 aa Tsp45I) digests 1 µg of pUC19 with the same pattern as native Tsp45I. This indicates that the second ORF of pTSp45s encodes Tsp45I endonuclease.

4. Re-cloning tsp45IM into pBR322, and tsp45IR into pACYC1 84-T7, to establish a stable Tsp45I R-M system which produces recombinant Tsp45I.

The Tsp45I R-M system is not stable in E. coli harboring pACYC184-tsp45IM and pET21a-tsp45IR plasmids. To generate a more stable system, the R-M genes are placed within different vectors. Specifically, tsp45IM is moved to a moderate-copy vector (pBR322) and expressed by the tetracycline resistance gene promoter. In addition, tsp45IR is moved to a low-copy vector (pACYC184), and still expressed by the strong inducible T7 promoter/lac operator of pET11a (pACYC184-T7).

The established tsp45IM is cloned via PCR into pBR322 in a method analogous to its cloning within pACYC184. The procedure and primers are identical to those used in cloning tsp45IM into pACYC184. Essentially, the SalI digested PCR product is introduced into the teracycline resistance gene of similarly cut pBR322. The host used is ER2566 (BL21 derivative, fhuA2 endA1, from New England Biolabs, Inc., Beverly, Mass.). Clones expressing M. Tsp45I are selected based on the resistance of their pBR322-tsp45IM plasmids to cleavage at nine sites by native Tsp45I. In the screening, 33% of transformants are resistant to Tsp45I digestion, indicating protection by cloned M.Tsp45I. Plasmid pBR322-tsp45IM should more completely modify and protect the *E. coli* genome (from cloned Tsp45I) than pACYC184-tsp45IM. This is due to its higher copy-number and hence higher overall predicted expression of M. Tsp45I.

The established tsp45IR is cloned via PCR in pACYC184-T7(+/−ter) vectors in both its 329 and 332 aa forms. The pACYC184-T7 vectors replace most of the tetracycline resistance gene with the EagI to HindIII fragment of pET-11a (Novagen, Inc., Madison, Wis.), which contains the strong inducible T7 promoter and lac operator. This promoter is identical to that in pET21a, but it is in a lower copy-number background. Therefore, overall background un-induced expression of Tsp45I should be lower in this vector than in pET21a-tsp45IR. The addition of four transcriptional terminators of rrnB (Kong et al., *J. Biol. Chem.* 268:1965–1975 (1993), (ter)) in pACYC184-T7 ter preceding the T7 promoter prevents any transcriptional read-through to the introduced tsp45IR.

Primers are generated to flank the tsp45IR with BamHI (5'-GGATCC-3') sites for cloning within pACYC184-T7 (+−ter). A preceding appropriately spaced RBS (5'-GGAGGT-3') is also placed in the forward primer to insure efficient expression from the T7 promoter. Forward primers are generated for both possible start codons. The forward (first eight codons) and reverse (last eight codons) primers are, respectively: 5'-CTAGGGATCCGG- AGGTT-TAAATAATGCAACAGATGGCCGAGTG GAAC-3' (332 aa) (SEQ ID NO:22) or 5'-CTAGGGATCCGGAGGTTTAAATAATGGCCGAGTGGAACGTGTGGACA-3' (329 aa) (SEQ ID NO:23), and 5'-CGCGGATCCTATTTAACTAGAGGCCCAGGGCTTCT TCACC-3' (SEQ ID NO:24).

The PCR reaction is carried out on 30 ng of YS45 plasmid DNA (30 cycles of 95° C. for one minute, 60° C. for one minute, and 72° C. for one minute) using Vent® DNA polymerase (New England Biolabs, Inc., Bevelry, Mass.). The expected approximately 1.0-kb PCR product is extracted from an agarose gel slice. The gel is digested with β-agarase according to the manufacturer's suggestions (New England Biolabs, Inc., Beverly, Mass.) and then precipitated. The PCR product is digested with BamHI for two hours, and then ligated to similarly cut/CIP treated pACYC184-T7 or pACYC184-T7ter. This introduces the PCR product downstream of the inducible T7 promoter.

The ligated DNA is then used to transform ER2566 cells harboring pBR322-tsp45IM. Clones are isolated on 30 μg/ml chloramphenicol and 100 μg/ml ampicillin plates at 30° C. (to reduce un-induced T7 activity). Plasmid DNA is isolated from transformants and visualized on agarose gels for the presence of both pBR322-tsp45IM and pACYC184-T7(+/−ter)-tsp45IR. In the screening 56% of transformants contain both plasmids.

Overnight cultures of these transformants are diluted 1:1000 in LB media (30 μg/ml chloramphenicol, 100 μg/ml ampicillin) and grown for three to four hours at 30° C. (late log phase) prior to induction with 0.25 mM IPTG for an additional two hours at 37° C. Cells from these cultures are sonicated (in 10 mM Tris-Hcl, 10 mM β-mercaptoethanol, pH 8.0) to generate crude cell lysates. Dilutions of these lysates are used to digest 1 μg of pUC19 in vitro (four Tsp45I sites) at 65° C. for one hour. The digested pUC19 is then compared with that digested by Tsp45I produced directly from YS45 cells. A large number of the transformants (33%) show Tsp45I activity, and are stable for multiple generations. These include both 329 and 332 aa versions of Tsp45I within either pACYC184-T7ter or pACYC184-T7.

One ER2566 transformant which stably harbors pBR322-tsp45IM and pACYC184-T7-tsp45IR (329 aa form) expresses about $3 \times 10^5$ units of recombinant Tsp45I per gram of wet cells upon induction. Therefore the plasmid-borne thermophilic Tsp45I R-M system is stably maintained in *E. coli*, and expresses high levels of recombinant Tsp45I.

A sample of the *E. coli* containing ER2566 [pBR322-tsp45IM, pACYC-T7-tsp45IR] (NEB # 1086) has been deposited under the terms and conditions of the Budapest Treaty with the American Type Culture Collection on Oct. 15, 1997 and received ATCC Accession Number 98556.

What is claimed is:

1. Isolated DNA coding for the Tsp45I restriction endonuclease gene (tsp45IR) wherein the isolated DNA is obtainable from the thermophilic eubacterium Thermus species YS45.

2. A mesophilic vector which includes the isolated DNA of claim 1.

3. A recombinant vector comprising a vector into which the isolated DNA of claim 1 has been inserted which has a thermophilic origin of replication and can transform an E. coli host cell.

4. The isolated DNA of claim 1 which contains the Tsp45I restriction endonucleases and methylase genes.

5. A recombinant vector comprising a vector that contains tsp45IR gene.

6. Isolated DNA coding for the Tsp45I restriction endonuclease and methylase, wherein the isolated DNA is obtainable from ATCC No.98556.

7. A recombinant vector comprising a vector that contains tsp45IM.

8. A host cell transformed by the vector of claims 2, 3, 5 or 7.

9. A method for producing Tsp45I restriction endonuclease comprising culturing the host cell of claim 8 under conditions suitable for expression.

10. A method for cloning a restriction endonuclease and methylase gene which comprises:

(a) purifying the plasmid DNA of Thermus species YS45;
    (b) digesting the DNA with a series of restriction endonucleases to generate fragments;
    (c) mapping the plasmids to define location of genes within the plasmid based on the digestion pattern;
    (d) ligating the digested plasmid DNA into a mesophilic cloning vector;
    (e) transforming a host cell with the vector of step (d);
    (f) mapping the transformed colonies of step (e) by introducing endonucleases;
    (g) sequencing the DNA of recombinant clones to match that of the thermophilic plasmid map;
    (h) identyfying the methylase gene from the sequenced plasmid map of step (g) and amplyfying, and cloning that DNA into an appropriate vector within E. coli; and
    (i) identifying the restriction gene from the sequenced plasmid map of step (g) and amplifying, and cloning that DNA into an appropriate vector within E. coli.

11. A method for producing Tsp45I restriction endonuclease comprising culturing a host cell transformed with the cloning vector of claim 10 step (I) under conditions suitable for expression of said endonuclease.

12. A method for producing Tsp45I recombinant restriction endonuclease which recognizes the base sequence in double-stranded DNA molecules:5'-GTGAC-3' and 5'-GTCAG-3' and cleaves the DNA before the first G in this site leaving five nucleotides as single stranded 5' overhangs at each end of the cleaved DNA comprising cluturing a host cell transformed with a cloning vector under conditions suitable for expression of said endonuclease, wherein the cloning vector comprises isolated DNA obtainable form thermophilic eubacterium Thermus species YS45.

* * * * *

UNITED STATES PATENT AND TRADEMARK OFFICE
CERTIFICATE OF CORRECTION

PATENT NO. : 5,866,422                                        Page 1 of 4
DATED      : February 2, 1999
INVENTOR(S) :
             Wayne, et al.

It is certified that error appears in the above-identified patent and that said Letters Patent is hereby corrected as shown below:

Column 1, line 35, replace "₂nd" with --$2^{nd}$--

Column 1, line 42, replace "Hjörleifsóttir" with --Hjörleifsdóttir--

Column 2, line 19, replace "₂nd" with --$2^{nd}$--

Column 2, line 53, replace "Pst1" with --PstI--

Column 2, line 61, replace "fYS40" with --φYS40--

Column 3, line 16, replace "DEVOS" with --DEVos--

Column 3, line 42, replace "'avoided" with --avoided--

Column 3, line 50, replace "E coli" with --E. coli--

Column 4, line 34, replace "pUC1 9-derived" with --pUC19-derived--

Column 4, line 37, replace "Xba1" with --XbaI--

Column 4, line 44, replace "₂nd" with --$2^{nd}$--

Column 4, line 60, replace "TthHB81" with --TthHB8I--

Column 4, lines 61-62, replace "NgoPI-M.NgoPII" with --M.NgoPII--

Column 5, line 16, replace "Pst1" with --PstI--

UNITED STATES PATENT AND TRADEMARK OFFICE
CERTIFICATE OF CORRECTION

PATENT NO. : 5,866,422

DATED : February 2, 1999

INVENTOR(S) : Wayne, et al.

It is certified that error appears in the above-identified patent and that said Letters Patent is hereby corrected as shown below:

Column 5, line 52, replace "pET21 a-tsp45IR" with --pET21a-tsp45IR--

Column 5, line 54, replace "pET21 a-tsp45IR" with --pET21a-tsp45IR--

Column 5, line 63, replace "pET21 a-tsp$%IR" with --pET21a-tsp45IR--

Column 6, line 41, replace "(X)" with --(λ)--

Column 6, line 3, replace "T7-(+" with --T7(+--

Column 7, line 64, replace "Westerfield" with --Westfield--

Column 8, line 23, replace "Pst1" with --PstI--

Column 8, line 28, replace "Pst1" with --PstI--

Column 8, line 29, replace "Psf1" with --PstI--

Column 8, line 36, replace "₂nd" with --2$^{nd}$--

Column 8, line 46, replace ":6); 5'GTGGGGTGGGCTGATAATCAA" with --:6); 5'G̲TGGGGTG̲GGCTGATAATCAA--

Column 8, line 48, replace "GATCAGCCCACCCCAC-3'" with --GATCAGCCC̲ACCCC̲AC-3'--

UNITED STATES PATENT AND TRADEMARK OFFICE
CERTIFICATE OF CORRECTION

PATENT NO. : 5,866,422
DATED : February 2, 1999
INVENTOR(S) : Wayne, et al.

Page 3 of 4

It is certified that error appears in the above-identified patent and that said Letters Patent is hereby corrected as shown below:

Column 9, line 3, replace "10 M.EcaI" with --M.EcaI--

Column 10, line 4, replace "pET21 a's" with --pET21a's--

Column 10, line 22, replace "pET21 a" with --pET21a--

Column 10, line 23, replace pET21 a's" with --pET21a's--

Column 10, line 30, replace "pACYCI 84" with --pACYC184--

Column 10 line 44, replace "Tris -Hcl" with --Tris-HCl--

Column 10, line 53, replace "pTSp45s" with --pTsp45s--

Column 10, line 55, replace "pACYC1 84-T7" with --pACYC184-T7--

Column 11, line 31, replace "(t- -ter)" with --(t/-ter)--

Column 12, line 18, replace "T7(+/- -ter)" with --T7(+/-ter)--

Column 12, line 26, replace "8-mercaptoethanol" with --ß-mercaptoethanol--

Column 12, line 26, replace "Hcl" with --HCl--

UNITED STATES PATENT AND TRADEMARK OFFICE
CERTIFICATE OF CORRECTION

PATENT NO. : 5,866,422
DATED : February 2, 1999
INVENTOR(S) : Wayne, et al.

It is certified that error appears in the above-identified patent and that said Letters Patent is hereby corrected as shown below:

Column 30, line 45, replace "identyfying" with --identifying--

Column 30, line 46, replace "amplyfying" with --amplifying--

Column 30, line 53, replace "(I)" with --(i)--

Column 30, line 60, replace "cluturing" with --culturing--

Column 30, line 63, replace "form" with --from--

Signed and Sealed this

Thirty-first Day of August, 1999

Attest:

Q. TODD DICKINSON

*Attesting Officer*     *Acting Commissioner of Patents and Trademarks*